(12) United States Patent
Harris et al.

(10) Patent No.: US 6,664,065 B2
(45) Date of Patent: Dec. 16, 2003

(54) MEASURING VIRAL REVERSE TRANSCRIPTASE ACTIVITY

(76) Inventors: Robert B. Harris, 3412 Walkers Ferry Rd., Midlothian, VA (US) 23112;
Thomas R. Reynolds, 14102 Waters Edge Ct., Midlothian, VA (US) 23112

(*) Notice: Subject to any disclaimer, the term of this patent is extended or adjusted under 35 U.S.C. 154(b) by 7 days.

(21) Appl. No.: 10/048,936

(22) PCT Filed: Jun. 21, 2001

(86) PCT No.: PCT/US01/19763
§ 371 (c)(1),
(2), (4) Date: Apr. 24, 2002

(87) PCT Pub. No.: WO01/98541
PCT Pub. Date: Dec. 27, 2001

(65) Prior Publication Data
US 2002/0192641 A1 Dec. 19, 2002

Related U.S. Application Data
(60) Provisional application No. 60/212,815, filed on Jun. 21, 2000.

(51) Int. Cl.$^7$ ............ C12Q 1/68; C12Q 1/70; C07H 21/04
(52) U.S. Cl. ............ 435/6; 435/5; 536/23.72
(58) Field of Search ............ 435/5, 6; 536/23.72

(56) References Cited
PUBLICATIONS
No revelant prior art was found.*
* cited by examiner

*Primary Examiner*—Hankyel T. Park
(74) *Attorney, Agent, or Firm*—Foley & Lardner

(57) ABSTRACT

In clinical settings as well as in a drug-discovery context, the impact of an agent that may affect reverse transcriptase (RT) can be measured and even quantified by bringing a sample, which may contain an RT, into contact with an RNA template, a primer complementary to the RNA template, and appropriate oligonucleotide-specific primers, under conditions such that they react, in the presence of RT, to form a cDNA product in inverse proportion to the effect of the agent. The amount of any resultant cDNA product then can be measured. The approach is readily implemented as a real-time, quantitative kinetic assay for RT activity.

14 Claims, 3 Drawing Sheets

MEASURING VIRAL REVERSE TRANSCRIPTASE ACTIVITY

FIELD OF THE INVENTION

The present invention relates generally to the detection of reverse transcriptase activity and, more particularly, to measuring viral reverse transcriptase quantitatively, in real time, in the context of drug screening as well as clinical testing.

BACKGROUND OF THE INVENTION

Silver et al., *Nucleic Acids Res.* 21: 3593 (1993), disclose an approach to detect a retrovirus, in a biological sample, by PCR amplification of the cDNA product of viral reverse transcriptase (RT). By this approach, a cDNA product is synthesized only if viral RT is present, and that cDNA then is detected by a conventional technique for identifying the presence of a DNA. Techniques for this purpose include, for example, Southern blot hybridization, visualization by ethidium bromide staining, measurement of incorporated radiolabeled nucleotides, and immunoassaying for a detectable moiety bound to the amplified DNA.

The techniques of product-enhanced reverse transcriptase assay (PERT, a/k/a "Amp-RT") and polymerase chain-reaction-based reverse transcriptase assay (PBRT) also have been employed to detect retroviral contamination, given their $10^6$-fold enhanced sensitivity, relative to conventional RT assays. Thus, the FDA Center for Biologics Evaluation and Research (CBER) has recommended PERT assays for screening patients for the presence of RT, and additionally for screening viral vaccine and gene-therapy preparations for RT contamination. Also, U.S. Pat. No. 5,849,494 describes the use of these methods for assaying the presence of human immunodeficiency virus (HIV) in a biological sample. On the other hand, PERT and PBRT present significant drawbacks in a clinical setting, because these methods are laborious and cannot be effected in real time.

The application of TaqMan® technology (PE Biosystems), in conjunction with a standard PCR-RT protocol for presence of RT, is well-established for the quantitative measurement of reverse transcriptase. See Ringel et al., *J. Clin. Endocrinol. & Metabolism* 84: 4037 (1999). Detection of RT activity with the TaqMan® technique can be effected rapidly and relatively safely. The TaqMan® technique further represents an advance over previous methodology because of its considerably increased sensitivity over conventional RT assays, the ability to shorten measurement time to within six hours, while eliminating the need for toxic chemicals such as radioisotopes and ethidium bromide.

Lovatt et al., *J. Virological Methods* 82: 185 (1999), report using TaqMan® PCR technology to detect and quantify viral contamination, in unknown samples, in the laboratory setting. Although the TaqMan® technique is employed in the laboratory setting, it apparently has not been used to detect HIV reverse transcriptase. Furthermore, although reverse transcriptase is known to be inhibited by various drug agents, a method of monitoring such agents' effectiveness by assaying RT is lacking in the clinical setting.

SUMMARY OF THE INVENTION

It is therefore an object of the present invention to provide an approach, for detecting viral RT, which is readily adapted to clinical use.

It is another object of the present invention to provide for the real-time monitoring of RT amplification products via a methodology that is particularly suited to testing agents for RT-affecting activity, e.g., in a high-throughput screening environment.

It is a further object of the present invention to assess, via the monitoring of viral RT activity, the efficacy of an anti-HIV or other anti-viral drug or putative therapeutic agent.

It is similarly an object of the invention to provide a diagnostic technique which can be performed in a clinical setting, rapidly and safely, to identify a range of pathogens of common medical concern.

It is still another object of the present invention to detect the presence of RT that is resistant, or to measure the level of resistance, to a known RT inhibitor.

In accomplishing these and other objectives, there has been provided, in accordance with one aspect of the invention, a method for measuring the presence of RT in a sample. The sample is tested for the presence of RT by contacting the sample with (i) an RNA template, such as polyadenylated RNA, (ii) a primer that is complementary to the RNA template, for example, oligo-dT, and (iii) a plurality of oligonucleotide-specific primers, at about a temperature preferably less than the deactivation temperature of the RT, which is typically in the range of about 37° C. for HIV RT. If RT is present in the sample, then cDNA is produced and can be detected accordingly.

In another embodiment of the present invention, a method is provided for measuring the effect of a test agent on the activity of an RT in a sample. The sample, which may contain an RT, is brought into contact with an RNA template, preferably human, a complementary primer, and plurality of oligonucleotide-specific primers such that cDNA is formed only if RT is present in the sample in an amount inversely proportional to the effect of said test agent. The sample is preferably taken from a human patient and is tested in the presence of HIV RT in real time in a clinical setting.

In this vein, one skilled in the art will understand that RT in a sample, preferably from a patient, can be tested to determine whether the RT in the sample has developed resistance to a known RT inhibiting test agent. This can be accomplished by measuring the effect of a known RT inhibiting test agent on the activity of RT in a sample, comparing that activity against the activity of RT in the absence of the known RT inhibitor and/or the activity of the RT in the presence of an RT inhibitor which is known to completely inhibit the RT activity of the sample.

Other objects and advantages of the invention will become apparent by review of the detailed description of preferred embodiments.

DETAILED DESCRIPTION OF THE PREFERRED EMBODIMENTS

Figure 1:
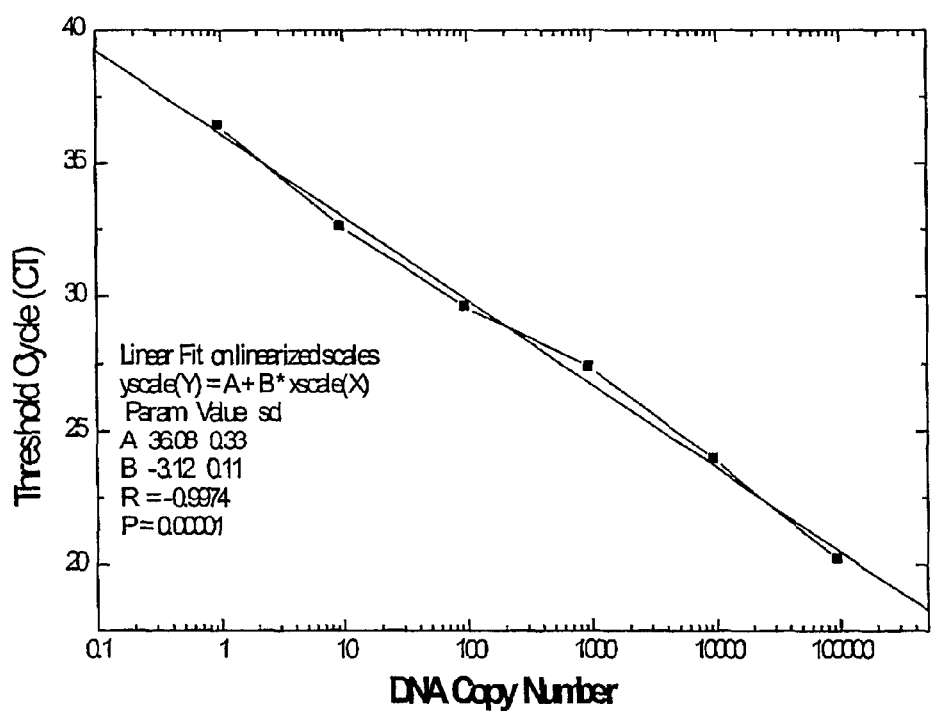
FIG. 1 shows a cDNA calibration curve.

In a preferred embodiment of the present invention, determining the presence of RT in a sample, such as a biological sample from a patient, entails introducing the sample to a reaction mixture that contains total human heart poly adenylated RNA, oligo-dT primer and dNTPs. If RT is present in the sample, then it will transcribe cDNA that corresponds to the total human heart poly A-RNA. Conversely, no cDNA product will be formed if RT is absent from the sample. Formation of any cDNA will be proportional to the concentration of any active RT present in the sample.

In accordance with the present invention, formation of cDNA, by virtue of the presence of RT in the sample, is followed by amplification and detection of the cDNA, preferably by means of a Taqman® technique well known in the art. It also is possible to detect the amplified cDNA product by other techniques well known in the art, including, but not limited too, Southern blot hybridization, ethidium bromide staining, measurement of incorporated radiolabeled nucleotides, immunoassaying for a detectable moiety bound to the amplified DNA, and measurement of fluorescence.

The present invention is applicable to measuring RT enzyme for a broad range of pathogens. Thus, the method can be employed in relation to all RNA viruses including, without limitation, retroviruses, flaviviruses, and yellow fever viruses. Illustrative flaviviruses in this regard are the West Nile virus and the encephalitis viruses, such as those strains associated with St Louis encephalitis, western equine encephalitis, Japanese equine encephalitis, and tick borne encephalitis.

Because the Taqman® assay is sensitive down to 10 copies of DNA, it is several log fold more sensitive than conventional PCR protocols, including gel based separations of the PCR amplicon. Further, the Taqman® assay is amenable to rapid throughput, and allows for determination of both RT activity and inhibition of RT activity, as described below.

The underlying basis for the Taqman® assay is that taq polymerase possesses both endonuclease and polymerase activities. Once the cDNA is formed by the action of RT, oligonucleotide-specific primers are used for the amplification aspect of PCR. Hybridizing "between" the primers on the cDNA, the Taqman® probe contains a reporter fluor, which can be FAM, at the 5' end of the oligonucleotide, and a quencher dye, which can be TAMRA, at the 3' end of the probe. The probe itself is not fluorescent, due to intramolecular fluorescence quenching. Thus, when the probe is intact, the proximity of the reporter fluor to the quencher dye results in suppression of the reporter fluorescence, primarily by Forster-type energy transfer. As the PCR proceeds, amplification of the target cDNA occurs and the DNA polymerase, during extension of the primer sequences, effects the 5' cleavage of the probe reporter, resulting in a reversal of quenching of fluorescence of the reporter and, hence, in a measurable fluorescent signal of cDNA production.

The cycle number at which the fluorescence emission of the PCR reaction exceeds the background fluorescence level is referred to as the threshold cycle ($C_T$) value and is calculated in real time. The $C_T$ value is dependent upon both the amount of PCR template and cDNA present in the reaction mixture. Thus, the RT activity in the sample can be quantified by comparing the $C_T$ value of an unknown, measured sample against the $C_T$ value of sample, run under the same conditions, having a known amount of cDNA.

In a preferred embodiment, the Taqman® protocol is used to detect the presence of recombinant HIV (rHIV) RT. In this regard, oligo dT is used as a template for rHIV RT. Oligo dT is complementary to the polyadenylated RNA-component of the total human heart RNA which present in the reaction mixture. rHIV RT forms cDNA from the oligo dT/RNA complex in the presence of dNTP nucleotides. If a patient sample is to be tested for the presence of HIV RT, an extract prepared from the patient sample is added, in place of rHIV-RT.

Some RTs tend to be heat-sensitive, and so the reaction described above must be performed under cycling conditions which do not destroy the activity of the RT, which occurs at a temperature of about 37° C. for rHIV RT, for example. Thus, the temperature cycling conditions for rHIV RT were about 25° C. for 10 minutes, followed by about 37° C. for 60 minutes, and finally 95° C. for 5 minutes. At 95° C., the activity of rHIV RT was destroyed. Note that the standard Taqman® temperature cycling conditions will also destroy the activity of rHIV RT. Typically, this aspect of the protocol is effected outside of the Taqman® instrument on a programmable PCR thermocycler.

Next, an aliquot of the cDNA formed in the RT step above is brought into the Taqman® instrument (PE Model 7700) and put into a reaction mixture which contains Taqman® Universal master mix (taq polymerase in buffer), beta actin-specific forward primer, beta actin-specific reverse primer, and beta actin Taqman® probe. The PCR step takes place in the instrument under standard Taqman® PCR conditions. Although, as described above, the present method is depicted as a two test tube reaction, one skilled in the art will realize that these steps can be combined in a single reaction vessel.

In another embodiment of the present invention, efficacy is ascertained for a test agent that can inhibit the activity of RT. In this context, the test agent preferably is added when the template RNA, the primer which is complementary to the template RNA, and the dNTPs are mixed in the presence of the sample. Accordingly, although the sample may contain active RT, cDNA transcription by the RT can be inhibited by the presence of the test agent in the reaction mixture.

The inhibiting properties of the test agent are reflected in an increase in $C_T$ value for the sample which contains the test agent. The more potent the inhibition of RT activity by the test agent, the higher the $C_T$ value from the Taqman® assay, measured against a control reaction containing no test agent. Because RT inhibition can be measured in real time, the present invention is optimally suited for real time drug screening of test agents which may have potential RT inhibiting properties. Additionally, the present method can be performed utilizing a biological sample from a patient with different known RT inhibiting agents, e.g., nucleoside and nucleotide analogs and non-nucleoside reverse transcriptase inhibitors, or combinations thereof, to screen and measure the patient RT for resistance against these RT inhibiting drugs in real time, thus leading to more informed drug dosage and dispensation.

In a clinical setting, in situ measurement of the efficacy of test agents allows for higher throughput of samples and subsequent efficiency in targeting promising test agents which exhibit inhibiting activity. Thus, purification of inhibiting agents can be tracked in addition to determining and quantitating the specific activity of the inhibiting agents. Similarly, drug choices for patients who may have built up resistance to specific drugs can be assayed without resulting in a loss of treatment time that can result from drug experimentation performed to determine if the patient evinces resistance. Toxicity and side effects of drugs on patients can further be limited as dosage testing of inhibiting agents can be performed to determine the optimal dosage of the inhibiting drug.

Additionally, the present invention can be performed, ex vivo, in a clinical setting on human patients. Because the present invention can be performed ex vivo, the activity of RT and efficacy of test agents is determined in a way that is non-toxic to the patient. As noted before, because the present invention measures RT activity or inhibition thereof in real time, assaying patient samples for the presence of specific pathogens can be performed in an extremely prompt manner, typically less than one hour.

The following, non-limiting example further illustrates advantages of the present invention. These solutions were employed in the protocol:
1. TaqMan® RT Reagent kit, which contains 10× reaction buffer, magnesium chloride stock solution, and RNAse inhibitor—Perkin Elmer catalogue No. N808-0234;
2. rHIV RT—Worthington Biochemical catalogue No. 5006 (500 U at 12.5 U/µL);
3. Total Human Heart RNA—Ambion catalogue No. 7966 (100 µg at 1 mg/ml);
4. 100 mM dNTP Mix (25 mM each NTP)—Perkin Elmer catalogue No. N808-0261;
5. Oligo dT (17-mer);
6. Random Hexamer (oligo (dNTP)6);
7. 2× TaqMan® Universal Master Mix—Perkin Elmer catalogue No. PE 4304437;
8. TaqMan® Beta Actin Reagents, which includes specific forward and reverse oligonucleotide primers for beta actin, plus the TaqMan® probe for beta actin—Perkin Elmer catalogue No. 401846; and
9. Beta Actin Plasmid DNA (American Type Tissue Culture catalogue No. 769559R).

A solution of 10 mM dNTP was prepared by diluting 1:10 dilution of 100 mM dNTP solution using water as the diluent. A 50 µM stock solution of oligo dT in water also was prepared.

An rHIV RT solution (Master Mix solution) was prepared which contained 5 µL 10× RT reaction buffer, 11 µL 25 mM MgCl$_2$, 10 µL 10 mM dNTP working stock solution, 2.5 µL 50 µM oligo dT, 1 µL RNAse inhibitor and 1.25 µL rHIV RT. The total volume of the Master Mix solution was 30.75 µL. Alternatively, random hexamer may be added in place of oligo dT. Oligo dT is the preferred primer, however.

Water plus test agent (totaling 18.25 µL) plus 1 µL total human heart RNA, for example:

1 µL test agent+17.25 µL water+1 µL total human heart RNA;
2 µL test agent+16.25 µL water+1 µL total human heart RNA;
5 µL test agent+13.25 µL water+1 total human heart µL RNA;
10 µL test agent+8.25 µL water+1 total human heart µL RNA;
15 µL test agent+3.25 µL water+1 total human heart µL RNA, were added to 30.75 µL of the Master Mix solution. Thus, the reaction mixture contained 50 µL total solution volume.

The controls for the present example included a positive control containing 18.25 µL water plus 1 µL RNA, and a negative control containing 19.25 µL water.

The transcriptase reaction was initiated by placing the reaction mixture in a MWG Thermocycler, or equivalent, under thermocycling conditions at 25° C. for 10 minutes, then at 37° C. for 60 minutes, and finally at 95° C. for 5 minutes. This final thermocycling step deactivated the rHIV RT. Next 5 µL of the post-thermocycle RT reaction mixture, which presumably contained cDNA, were added to 45 µL of the Master Mix solution. The Master Mix Solution contained 25 µL 2×Taqman Universal Master Mix, 5 µL beta Actin Forward Primer, 5 µL Beta Actin Reverse Primer and 5 µL water. Thus, the total PCR reaction mixture contained 50 µL.

The PCR reaction was carried out in the Perkin Elmer 7700 TaqMan instrument, as recommended by the manufacturer, under the following conditions: at 50° C. for 2 minutes; then at 95° C. for 10 minutes. 40 cycles were then performed at 95° C. for 15 seconds followed by 60° C. for 1 minute. Upon completion, the data were plotted and visualized as described in the Perkin Elmer 7700 TaqMan instrument manual.

Increase in fluorescence was monitored as a function of cycle number. The data was presented as relative fluorescence versus $C_T$. A correlation between $C_T$ value and number of copies of DNA was determined from a calibration curve prepared using a known amount of DNA. For this determination, beta Actin DNA was used in place of the RT reaction mixture in the PCR reaction step. The useful range of beta actin DNA with which to prepare the calibration curve was 5 ag (atograms) which corresponds to approximately 1 copy of DNA to 500 fg (femtograms) which corresponds to $9.5 \times 10^4$ copies of DNA.

The number of copies of DNA was based on the following observation: One microgram (1 µg) of PBR322 plasmid DNA is equivalent to 36 pmol of PBR 322 plasmid DNA ($2.2 \times 10^{11}$ copies of DNA). PBR322 plasmid DNA encompasses 4360 bp. Beta actin plasmid DNA encompasses 5000 bp.

The TaqMan® calibration curve is shown in FIG. 1. In the figure, known amounts (known copy numbers) of beta-actin DNA were used for the PCR component of the assay protocol and the observed threshold value ($C_T$) recorded. Note that with decreasing copy number, the $C_T$ value becomes prolonged. The calibration curve assay is linear down to at least 1 copy of DNA and extends to at least 100,000 copies of DNA. The curve was fit by apparent linear regression (this is a linear/log plot) and shows a regression fit of 0.99. The equation of the line is Y=−3.12(X)+36, where X is the DNA copy number and 36 is the $C_T$ value at infinitely low (less than one) copy of DNA.

In the EXAMPLES below, the above protocol was used, with minor modifications which will be obvious to one skilled in the art.

EXAMPLE I

Figure 2:
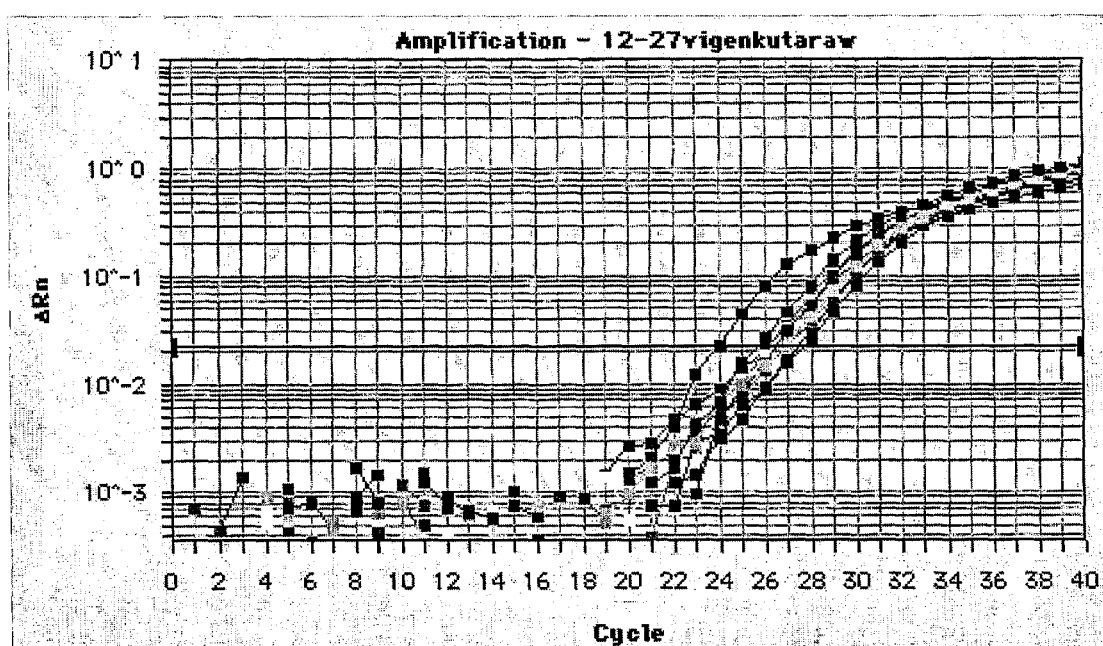
FIG. 2 depicts the inhibition of rHIV RT by increasing concentrations of test agent.

Example I illustrates the increase in fluorescence as a function of cycle number using a test agent in increasing final concentrations of 0, 1%, 5%, 10% (v/v). The $C_T$ value of the positive control is indicated by a horizontal black line. This $C_T$ value is the midpoint of the increase in fluorescence above background. As illustrated in FIG. 2, the positive control sample showed a $C_T$ value of 24 cycles. The remaining curves of FIG. 2 demonstrate inhibition of rHIV RT in the presence of a test agent proprietary to applicant. At higher concentrations of test agent, the $C_T$ value became increasingly larger, indicating that the rHIV RT activity was being progressively inhibited.

EXAMPLE II

Figure 3:
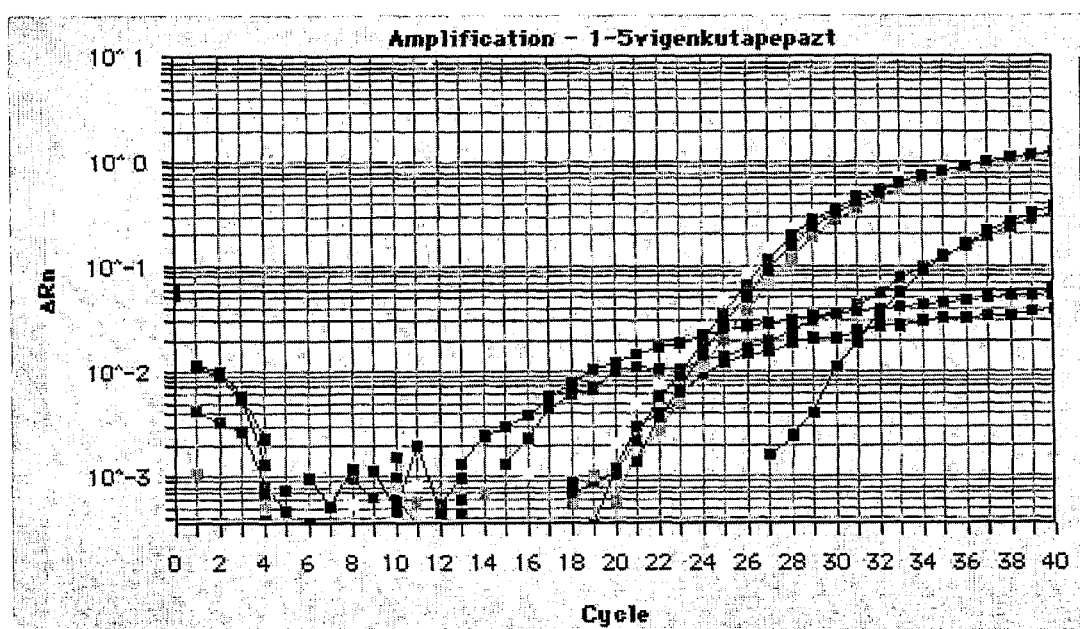
FIG. 3 similarly depicts the inhibition of rHIV RT by increasing concentrations of test agent.

Another example of rHIV RT inhibition in the presence of a second anti-viral test agent proprietary to applicant. As shown in FIG. 3, samples that crossed the threshold at $C_T$ 26 are the RT PCR control (no test agent) and 1% (v/v) test agent (as final concentration in the RT reaction mixture). The 5% (v/v) test agent sample crossed the threshold at cycle 33 and the 10% (v/v) test agent never crossed threshold, indicating 100% inhibition of rHIV RT activity.

Inhibition caused by the test agent can be expressed in terms of the number of copies of DNA present in the PCR reaction mixture. Thus:

| Sample | CT | # Copies DNA | % Inhibition |
|---|---|---|---|
| Control | 26 | 1701 | 0 |
| 1% test agent | 26 | 1701 | 0 |
| 5% test agent | 33 | 10 | 99.4 |
| 10% test agent | >40 | 0 | 100 |

EXAMPLE III

The following example demonstrates the inhibition efficacy of AZT on a sample containing rHIV RT AZT (a nucleotide analog of dT) in the range of 250 μM to 1.25 mM was added to the rHIV-RT reaction mixture in place of dT. When the AZT was added, no amplification of cDNA was observed after the PCR step. Similarly, when AZT was included in the PCR reaction mixture in place of dT, NO amplification of the cDNA was seen after the PCR step.

Finally, decreasing concentrations of AZT were added to the RT reaction mixture in the presence of a fixed concentration of dT. The final AZT concentration ranged from 1.25 mM down to 250 μM. At all concentrations of AZT, the observed $C_T$ was greater than 40 cycles, indicating 100% inhibition of activity.

While preferred embodiments have been illustrated and described, it should be understood that changes and modifications can be made therein in accordance with one of ordinary skill in the art without departing from the invention in its broader aspects as defined in the following claims.

What is claimed is:

1. A method for measuring the effect on reverse transcriptase of an agent affecting a sample that may contain a reverse transcriptase, comprising
   (a) bringing said sample into contact with template RNA, a primer complementary to said template RNA, and a plurality of oligonucleotide-specific primers under conditions such that they react, in the presence of a reverse transcriptase, to form a cDNA product in inverse proportion to the effect of said agent, and
   (b) measuring the amount of said cDNA product.

2. The method of claim 1, wherein the template RNA is a polyadenylated RNA and the primer complementary to said template RNA is an oligo-dT primer.

3. The method of claim 1, wherein step (b) comprises amplifying said cDNA product and then measuring said amount in relation to cDNA product obtained in the absence of said agent.

4. The method of claim 2, wherein said polyadenylated RNA is human RNA.

5. The method of claim 2, wherein said conditions include a reaction temperature of 37° C. or less.

6. The method of claim 3, wherein said reverse transcriptase is an HIV reverse transcriptase.

7. The method of claim 3, wherein said reverse transcriptase is recombinant HIV reverse transcriptase.

8. The method of claim 3, wherein said sample is comprised of biological material infected by HIV.

9. The method of claim 2 wherein step (a) is preceded by obtaining said sample from a patient.

10. The method of claim 3 wherein step (a) is preceded by obtaining said sample from a patient.

11. A method for measuring reverse transcriptase in a sample that may contain an HIV reverse transcriptase, comprising
    (a) bringing said sample into contact with template RNA, a primer complementary to said template RNA, and a plurality of oligonucleotide-specific primers under conditions such that they react, in the presence of a reverse transcriptase, to form a cDNA product, wherein said conditions include a reaction temperature less than about the deactivation temperature of said reverse transcriptase, and
    (b) detecting the presence of cDNA product.

12. The method of claim 10, wherein the template RNA is a polyadenylated RNA and the primer complementary to said template RNA is an oligo-dT primer.

13. The method of claim 11 wherein the reaction temperature is less than about 37° C.

14. The method of claim 10, wherein step (b) comprises amplifying and then measuring said cDNA product.

* * * * *